United States Patent
Blechman

(10) Patent No.: US 6,576,272 B1
(45) Date of Patent: *Jun. 10, 2003

(54) DIETARY SUPPLEMENT AND METHOD OF USING SAME

(75) Inventor: Steve E. Blechman, Poquott, NY (US)

(73) Assignee: Twin Laboratories Incorporated, Hauppauge, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,314

(22) Filed: Mar. 5, 1999

(51) Int. Cl.⁷ .................. A61K 35/78; A01K 65/00
(52) U.S. Cl. ............................ 424/736; 424/730
(58) Field of Search ................... 424/195.1, 730, 424/736

(56) References Cited

U.S. PATENT DOCUMENTS

| | | | | |
|---|---|---|---|---|
| 4,833,128 A | * | 5/1989 | Solomon et al. | 514/23 |
| 4,861,594 A | * | 8/1989 | Subbiah | 424/195.1 |
| 5,422,352 A | * | 6/1995 | Astrup | 514/264 |
| 5,798,101 A | * | 8/1998 | Haveson | 424/195.1 |

FOREIGN PATENT DOCUMENTS

| JP | 6-133731 | * | 5/1994 |
|---|---|---|---|
| WO | WO 98/14200 | * | 4/1998 |

OTHER PUBLICATIONS

Colker et al. Current Therapeutic Research Clinical and Experimental. Mar. 1999. vol. 60, No. 3, pp. 145–153.*
Naturade Products, Inc. Product Alert, (Jul. 3, 1989) pp. n/a.*
Product Alert, ( Nov. 24, 1997). Bodyonics Pinnacle Juncle Herbolics Dietary Supplement–ThermoPhen. STN database Promt 97:627029/an.*
Merck Index 12th Edition. 1674, p. 268.*
Product Alert, (Jul. 13, 1998) . Core Nutrition Shred Plus Supplement. STN database Promt 1998:344135/an.*
Product Alert, (Aug. 10, 1998). USA Nutritionals Metabo–Rise Capsules. STN databas Promt 1998:407946/an.*
Product Alert, (Feb. 8, 1999). Herbal Phen Trim Dietary Supplement. STN database Promt 1999:69348/an/.*
Product Alert, (May 25, 1998). Thin Phen Weight Loss Supplement. STN database Promt 1998:274466/an.*
Atkinson et al. Obesity Research. Nov. 4, 1995. vol. 3, Suppl.4, pp. 497S–500S.*

* cited by examiner

Primary Examiner—Irene Marx
Assistant Examiner—Vera Afremova
(74) Attorney, Agent, or Firm—Morgan & Finnegan, LLP

(57) ABSTRACT

Dietary supplements comprising *Citrus aurantium* extract and a methylxanthine, with or without St. John's wort extract and L-Phenylalanine for controlling weight wherein fat is lost and lean body mass preserved.

5 Claims, 2 Drawing Sheets

Figure 1
Baseline Characteristics

| Measure | Group A | Group B | Group C | p value |
|---|---|---|---|---|
| Age (years) | 38.0 (15) | 41.9 (9.1) | 57.8 (8.9) | 0.51 |
| Body Mass Index | 29.5 (2.8) | 28.8 (3.4) | 26.8 (1.7) | 0.34 |
| Weight (kg) | 90.9 (17.5) | 83.6 (17.5) | 78.1 (11.5) | 0.19 |
| Percent Body Fat | 26.3 (7.1) | 25.4 (5.6) | 23.2 (4.6) | 0.72 |
| Fat Mass (kg) | 24.6 (11.3) | 46.1 (6.05) | 17.8 (2.6) | 0.17 |
| Basal Metabolic Rate | 2026 (279) | 1908 (456) | 1859 (304) | 0.73 |
| Glucose (mg/dl) | 89 (18.2) | 86.1 (18.2) | 88 (17.9) | 0.77 |
| Cholesterol (mg/dl) | 216 (62) | 200 (45) | 209 (50) | 0.60 |
| Triglycerides (mg/dl) | 119 (65) | 169 (153) | 142 (88) | 0.47 |

Key: Values reported as averages with associated error in parentheses.
Body Mass Index = weight (kg)/height ($m^2$). Glucose, cholesterol and triglycerides are fasting values. Analysis of variance (ANOVA) used for three group comparisons.

Figure 2
Physical and Metabolic Changes

| Measure | Group | Baseline | Week Six | Percent Change | P value |
|---|---|---|---|---|---|
| Body Weight (kg) | | | | | |
| | *A | 90.9 (17.5) | 89.5 (16) | -1.5% | 0.05 |
| | B | 83.6 (17.5) | 82.7 (18) | -1.1% | 0.10 |
| | C | 78.1 (11.5) | 77.7 (10.5) | -0.05% | ns |
| Percent Body Fat | | | | | |
| | *A | 26.3 (7.1) | 23.4 (6.9) | -2.9% | 0.01 |
| | B | 24.4 (5.6) | 26.2 (4.8) | +1.8% | ns |
| | C | 23.2 (4.6) | 21.0 (3.7) | -2.2% | 0.10 |
| Fat Mass (kg) | | | | | |
| | *A | 24.6 (11.3) | 21.5 (10.1) | -13% | 0.01 |
| | B | 20.9 (6.1) | 21.5 (5.9) | +0.3% | ns |
| | C | 17.8 (2.6) | 16.0 (1.4) | -10% | 0.10 |
| Basal Metabolic Rate (calories/day) | | | | | |
| | *A | 2026 (269) | 2069 (268) | +3.0% | 0.05 |
| | B | 1908 (456) | 1868 (437) | -3.0% | 0.05 |
| | C | 1859 (304) | 1870 (300) | +0.1% | 0.10 |

Key: * = significant change as compared to the other groups; p<0.05.
Baseline and week six numbers reported as averages with associated error in parentheses. Paried t-tests used for changes over time. Repeated measures of analysis of variance (ANOVA) used to test time * group interaction to compare change over time between groups.

DIETARY SUPPLEMENT AND METHOD OF USING SAME

BACKGROUND OF THE INVENTION

1. Technical Field

The present invention relates generally to dietary supplements, and more particularly to a combination of *Citrus aurantium* extract and one or more ingredients designed to control weight via loss of fat and maintenance of lean body mass.

2. Background Art

Weight control is a concern of human beings. More and more individuals are joining health clubs, purchasing home exercise equipment and participating in sporting activities. In order to improve their performance in these activities, individuals may desire to lose body fat while at the same time maintaining or preserving lean body mass.

More importantly, excessive accumulation of body fat (i.e. obesity) can be dangerous and has been linked to health problems such as type II diabetes, hypertension, hyperlipidemia, coronary heart disease, stroke, breast and colon cancer, sleep apnea, gallbladder disease, gastroesophogeal reflux disease, fatty liver, gout, thromboembolism. Despite increased awareness of these health risks among Americans, the prevalence of obesity in the United States has more than doubled since the turn of the century. *The Merck Manual*, 15th ed. p. 952.

Determinants of obesity include social factors, psychologic factors, genetic factors, developmental factors, and decreased physical activity. Some components of a comprehensive weight loss program include medical assessment, behavior and dietary modification, nutrition education, cognitive restructuring, increased physical activity, and long term follow-up.

Unfortunately, losing weight (and keeping it off) is very difficult for most individuals. Weight gain results when an individual's caloric intake exceeds the number of calories expended as energy. In attempting to lose weight, an individual may utilize a regimen of caloric deficit (i.e. decreasing caloric intake so that calories expended as energy exceed caloric intake). Generally, the result is an adaptive response of a lowered basal (resting) metabolic rate. Caloric deficit can also cause a loss of skeletal muscle. Thus, weight loss or reducing caloric intake results in a lowering of resting energy expenditure and loss of lean body mass. This makes it harder to keep the weight off once the individual has attained his desired weight goal.

One cause of this decreased resting energy expenditure may be reduced functionality of the sympathetic nervous system (SNS) of the body. It has been observed that genetically obese rats exhibit low sympathetic outflow or responsiveness in various tissues. Humans genetically predisposed to weight gain already exhibit reduced SNS functioning; decreased energy expenditure further exacerbates their condition.

Physiologically, reduced SNS functioning translates into reduced adrenaline (norepinephrine and epinephrine) induced thermogenesis (i.e. reduced heat production within the body). One role played by norepinephrine and epinephrine in the body is the regulation of metabolism via stimulation of beta-adrenergic receptors within the SNS. Beta-adrenergic receptors are involved in the pathways of lipolysis (i.e. breakdown or hydrolysis of fats from fat stores into fatty acids), glycogenolysis (i.e. breakdown of glycogen into glucose) and thermogenesis. Thus, reduced SNS functioning impedes these pathways.

Indirect sympatheticomimetic compounds are adrenergic agents that potentiate (i.e. increase) the release of norepinephrine and epinephrine at pre-synaptic sites in the SNS and thereby avert reduced SNS functioning resulting from weight loss or reduced caloric intake. In the past, indirect sympatheticomimetic drugs such as ephedrine have been administered to humans as slimming agents, often in combination with methylxanthines (stimulatory agents) such as caffeine or theophylline. While individuals undergoing such treatment may lose weight, treated individuals may also experience undesirable side effects such as nervousness, tachycardia, hypertension, insomnia and dry mouth.

Thus, there exists a need in the art for an effective and safer dietary supplement that promotes weight loss and maintains lean body mass, while avoiding potential negative side effects associated with other dietary supplements used to promote weight loss.

BRIEF SUMMARY OF THE INVENTION

The invention includes: (a) a dietary supplement comprising *Citrus aurantium* extract and a methylxanthine, with or without St. John's wort extract and/or L-Phenylalanine; (b) a method of promoting weight loss by administration of the dietary supplement; and (c) a method of promoting fat loss while preserving lean body mass by administration of the dietary supplement. When administration of the dietary supplement is combined with caloric restriction and exercise, the degree of weight loss is greater than that experienced with caloric restriction and exercise alone.

Thus, an object of the invention is to promote weight loss. Another object of the invention to promote fat loss while maintaining or preserving lean body mass. An additional object of the invention is to avoid negative side effects associated with other dietary supplements used to promote weight loss (i.e. depression, nervousness, hypertension, etc.). Other objectives, advantages and features of the invention will become apparent from the following detailed description of the invention, and from the claims.

BRIEF DESCRIPTION OF THE DRAWINGS

FIG. 1 shows the baseline characteristics of subjects in the study described in the Example.

FIG. 2 shows the physical and metabolic changes of subjects in the study described in the Example.

DETAILED DESCRIPTION OF THE PREFERRED EMBODIMENT

The dietary supplements of the invention comprise *Citrus aurantium* extract (containing synephrine alkaloids) and a methylxanthine, preferably caffeine (such as from guarana seed extract), with or without St. John's wort extract and/or L-Phenylalanine.

Synephrine, an indirect sympatheticomimetic agent, is isolated from the *Citrus aurantium* genus. In a preferred embodiment of the invention, *Citrus aurantium* extract is standardized for about 4–6% synephrine alkaloids.

Guarana seed extract contains caffeine. The effects of caffeine include stimulating the central nervous system and increasing metabolic rate. In a preferred embodiment of the invention, guarana seed extract is standardized for about 22% caffeine.

St. John's wort contains hypericin, a natural compound that helps minimize the effects of minor to moderate depression. In a preferred embodiment of the invention, St. John's wort is standardized for about 0.3% hypericin.

L-Phenylalanine, an essential amino acid, is a pre-cursor to excitatory neurotransmitters in the brain—dopamine and norepinephrine. L-Phenylalanine replenishes neurotransmitters which control thermogenesis, mood, behavior and alertness.

Typical formulations of dietary supplements according to the invention include: dietary supplements wherein the molar ratio of synephrine alkaloids to caffeine is about 1:35 to 35:1; dietary supplements wherein the molar ratio of synephrine alkaloids to hypericin is about 1:36 to 36:1; dietary supplements wherein the weight ratio of *Citrus aurantium* extract to guarana seed extract is about 1:4 to 4:1; dietary supplements wherein the weight ratio of *Citrus aurantium* extract to St. John's wort is about 1:2 to 2:1. Typical formulations of dietary supplements according to the invention also include dietary supplements having: about 275 to 375 mg, preferably 325 mg, *Citrus aurantium* extract; about 0 to 400 mg, preferably 300 mg, St. John's wort extract; about 0 mg to 100 mg, preferably 50 mg, L-Phenylalanine; about 750 to 850 mg, preferably 800 mg, guarana seed extract. Typical daily dosages of the invention are: about 500 to 1000 mg, preferably 650 mg, *Citrus aurantium* extract; about 500 to 1000 mg, preferably 600 mg, St. John's wort extract; about 0 mg to 200 mg, preferably 100 mg, L-Phenylalanine; about 1000 to 2400 mg, preferably 1600 mg, guarana seed extract.

Common excipients of the dietary supplements of the invention include a thermogenic and herbal base blend containing *Coleus Forskohlii* (pashanabhedi) root extract, green tea extract, citrus bioflavinoids, ginger root, cayenne and yohimbe bark extract.

Synephrine alkaloids (from *Citrus aurantium* extract) are another indirect sympatheticomimetic agent. Like ephedrine, synephrine alkaloids are adrenergic, but potentiate the release of compounds which stimulate predominately beta-3-adrenergic receptors of the sympathetic nervous system (SNS). Synephrine alkaloids exert their effects via liberation of the compounds epinephrine, norepinephrine and dopamine from pre-synaptic sites in the SNS. Unlike ephedrine, synephrine alkaloids do not readily cross the blood-barrier barrier, due to their lesser level of lipophilicity. Thus, dietary supplements containing synephrine instead of ephedrine may offer a wider margin of safety. Furthermore, none of the side effects previously seen with investigations of ephedrine (i.e. nervousness, tachycardia, hypertension, insomnia and dry mouth) are exhibited upon ingestion of dietary supplements of the present invention.

The unique metabolism of *Citrus aurantium* extract predisposes this compound to thermogenesis: Dietary supplements of the present invention avoid lowered resting energy expenditure by preventing the decline in metabolic rate associated with a reduced calorie diet primarily by enhancing basal metabolism. *Citrus aurantium* extract also stimulates lipolysis and fat burning.

When *Citrus aurantium* extract is combined with a methylxanthine such as caffeine in the dietary supplements of the present invention, the thermogenic nature of the dietary supplement is further enhanced. In the absence of methylxanthines, thermogenic response may be limited. However, methylxanthines prolong thermogenesis by antagonizing adenosine and phosphodiesterases, thereby increasing epinephrine and sustaining activation of the beta-adrenergic receptor cell. Furthermore, octopamine (another alkaloid found within *Citrus aurantium* extract) has been shown to couple with alpha 2A-adrenoreceptors in a dose dependent manner, yielding a decrease in adenosine production.

Symptoms of depression are directly correlated to weight gain. Furthermore, depression may be a causative or reactive factor in the etiology of obesity. Thus, it is desirable not only to treat the obesity, but to treat the depression. Dietary supplements of the present invention may be used to treat depression by treating obesity. In particular, dietary supplements of the present invention including St. John's wort may be used to directly treat depression, while, at the same time, treating obesity or heaviness.

EXAMPLE

The effect of *Citrus aurantium* extract (an indirect β-sympatheticomimetic agent), caffeine, and St. John's wort on body composition, metabolic parameters, plasma lipid levels and mood states in overweight healthy adults was investigated. A double-blind randomized placebo-controlled protocol was employed.

Twenty-three subjects began the six-week study; twenty subjects finished. (Three subjects dropped out for reasons unrelated to the study.) Each subject was assigned to one of three groups: treatment (Group A-9 finishing), placebo (Group B-7 finishing), or control (Group C-4 finishing).

Each of the groups were similar in age, systolic and diastolic blood pressure, Profile of Mood States, body mass index, body weight, percent body fat, pounds of actual fat, lean body mass, basal metabolic rate, blood sugar, total cholesterol and triglycerides. There were no significant differences between the groups at baseline. FIG. 1 summarizes the Groups' baseline characteristics. Group A received 975 mg of *Citrus aurantium* extract (6% synephrine alkaloids), 528 mg of caffeine, and 900 mg of St. John's wort (0.3% hypericum) daily. Group B received a placebo (sugar pill). Group C received nothing. For the duration of the study, the subjects were instructed by a registered dietician on an 1800 calorie American Heart Association Step One diet. Each subject also followed a three day per week circuit training exercise program, supervised by an exercise physiologist, wherein each subject achieved 70% of his or her age predicted heart rate maximum (Karvonen formula) each exercise session.

Each subject was evaluated at baseline, week three, and week six for total body weight (Detecto™ balanced medical scale), body composition (Biodynamics v3.10, Seattle Wash. bioelectric impedance analyzer), feelings of vigor or fatigue (Educational and Industrial Testing Service, San Diego, Calif., Profile of Mood States questionnaire), biochemical data (SMAC-20 serum chemistries, complete blood count with differential, total cholesterol, and triglycerides, Quest Diagnostics, Wallingford, Conn.), electrocardiogram (Burdock Eclipse 800), and urinalysis (Chemstrip Analyzer, Indianapolis, Ind.).

Each group was tested for intergroup and intragroup variance. Paired T-tests were used for intragroup change over time and analysis of variance (ANOVA) was used to test for time/group interaction to compare change over time between groups. Significance was set at $p<0.05$.

A summary of the results of the study is set forth in FIG. 2. The results included the following: Only Group A experienced a significant decrease in overall body weight (1.4 kg; $p<0.05$). Group A also achieved a significant reduction in percent body fat (2.9%; $p<0.05$) and a significant decrease in actual fat loss (3.1 kg; $p<0.05$). Thus, lean body mass was preserved in Group A. While Group C showed a trend in percent body fat lost, Group C did not lose a significant amount of body fat (p=0.10). Group A also realized a significant increase in basal metabolic rate (from 2026 to 2069 calories/day; p<0.05). Group A experienced a trend in decrease of both plasma cholesterol and triglycerides (p=0.10). There were no significant changes in Profile of Mood States for fatigue or vigor in any of the three groups. There were also no significant changes in blood pressure, heart rate, electrocardiograms, serum chemistries or urinalysis in Group A.

Therefore, a dietary supplement containing *Citrus aurantium* extract, caffeine, and St. John's wort is safe and effective when combined with mild caloric restriction and exercise for promoting both weight and fat loss in healthy overweight adults while at the same time preserving lean body mass.

It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A method of promoting fat loss while preserving lean body mass, comprising the daily administration to a human of about 975 mg *Citrus aurantium* extract standardized for about 6% synephrine alkaloids, about 528 mg caffeine, and about 900 mg St. John's wort extract standardized for about 0.3% hypericum.

2. A method of promoting weight loss while preserving lean body mass, comprising the daily administration to a human of about 975 mg *Citrus aurantium* extract standardized for about 6% synephrine alkaloids, about 528 mg caffeine, and about 900 mg St. John's wort extract standardized for about 0.3% hypericum.

3. A method of promoting fat loss while preserving lean body mass, comprising the daily administration to a human of about 975 mg *Citrus aurantium* extract standardized for about 6% synephrine alkaloids, about 2400 mg guarana seed extract standardized for about 22% caffeine, and about 900 mg St. John's wort extract standardized for about 0.3% hypericum.

4. A method of promoting weight loss while preserving lean body mass, comprising the daily administration to a human of about 975 mg *Citrus aurantium* extract standardized for about 6% synephrine alkaloids, about 2400 mg guarana seed extract standardized for about 22% caffeine, and about 900 mg St. John's wort extract standardized for about 0.3% hypericum.

5. A dietary supplement, in capsule form, comprising about 325 mg *Citrus aurantium* extract standardized for about 6% synephrine alkaloids, about 800 mg guarana seed extract standardized for about 22% caffeine, and about 300 mg St. John's wort extract standardized for about 0.3% hypericum.

* * * * *